(12) United States Patent
Yonezu et al.

(10) Patent No.: US 9,970,910 B2
(45) Date of Patent: May 15, 2018

(54) GAS SENSOR AND METHOD OF MANUFACTURING GAS SENSOR

(71) Applicant: NGK Spark Plug Co., LTD., Nagoya (JP)

(72) Inventors: Kunihiko Yonezu, Inuyama (JP); Takehiro Oba, Kounan (JP); Hisaharu Nishio, Tokai (JP); Ginjiro Ito, Nagoya (JP); Yuichi Yamada, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 17 days.

(21) Appl. No.: 15/009,081

(22) Filed: Jan. 28, 2016

(65) Prior Publication Data

US 2016/0223505 A1 Aug. 4, 2016

(30) Foreign Application Priority Data

Jan. 30, 2015 (JP) ................... 2015-016280
Apr. 21, 2015 (JP) ................... 2015-086738
Nov. 18, 2015 (JP) ................... 2015-225419

(51) Int. Cl.
*G01N 33/00* (2006.01)

(52) U.S. Cl.
CPC ................. *G01N 33/0009* (2013.01)

(58) Field of Classification Search
CPC .............. G01M 15/102; G01N 33/0009
See application file for complete search history.

(56) References Cited

U.S. PATENT DOCUMENTS

| 6,068,746 | A |  | 5/2000 | Kojima et al. |
| 6,260,445 | B1 | * | 7/2001 | DeVecchis ............... B25B 15/02 81/438 |
| 8,337,132 | B2 | * | 12/2012 | Steffenfauseweh .. B60Q 1/0433 403/408.1 |
| 9,093,799 | B2 | * | 7/2015 | Kiribayashi ......... H01R 12/725 |
| 9,326,872 | B2 | * | 5/2016 | Sokel .................... A61F 2/95 |
| 9,335,311 | B2 | * | 5/2016 | Yonezu ............. G01N 27/4062 |
| 9,360,448 | B2 | * | 6/2016 | Yonezu .............. G01N 27/407 |
| 2005/0029101 | A1 | * | 2/2005 | Isomura ............ G01N 27/4077 204/428 |

(Continued)

FOREIGN PATENT DOCUMENTS

| JP | 3873390 B | 1/2007 |
| JP | 2013246004 A * | 12/2013 |

*Primary Examiner* — Harshad R Patel
*Assistant Examiner* — Punam Roy
(74) *Attorney, Agent, or Firm* — Leason Ellis LLP

(57) ABSTRACT

A gas sensor includes a gas sensor element that extends in an axial direction and that includes a detector, which detects a specific gas in a mixed gas; a metal shell that surrounds a periphery of the gas sensor element to hold the gas sensor element; a base that is disposed on a rear side of the metal shell and that covers a rear end portion of the gas sensor element, the base being made of a polymer material; and a metal tube that connects the metal shell and the base to each other and that includes a rear portion and a front portion, the rear portion being integrated with the base, the front portion forming an exposed portion that is exposed from the base. A part of the exposed portion of the tube is connected to the metal shell, and the base is disposed apart from the metal shell.

10 Claims, 6 Drawing Sheets

(56) References Cited

U.S. PATENT DOCUMENTS

| | | | |
|---|---|---|---|
| 2007/0220955 A1* | 9/2007 | Noda | G01N 27/4077 73/31.05 |
| 2011/0239740 A1* | 10/2011 | Fujita | G01N 27/4077 73/31.07 |
| 2011/0259084 A1* | 10/2011 | Atsumi | G01N 27/4067 73/31.05 |
| 2012/0018305 A1* | 1/2012 | Yoshikawa | G01N 27/4077 204/431 |
| 2012/0239271 A1* | 9/2012 | Tajima | F02D 41/1455 701/102 |
| 2013/0327121 A1* | 12/2013 | Shimazaki | G01N 27/4077 73/23.2 |
| 2014/0020446 A1* | 1/2014 | Yonezu | G01N 27/4062 73/23.2 |
| 2017/0052140 A1* | 2/2017 | Yonezu | G01N 27/409 |

* cited by examiner

GAS SENSOR AND METHOD OF MANUFACTURING GAS SENSOR

This application claims the benefit of Japanese Patent Applications No. 2015-016280 filed Jan. 30, 2015, No. 2015-086738 filed Apr. 21, 2015 and No. 2015-225419 filed Nov. 18, 2015, all of which are incorporated herein by reference in its entity.

BACKGROUND OF THE INVENTION

1. Field of the Invention

The present invention relates to a gas sensor including a gas sensor element for detecting the concentration of a gas to be detected and a method of manufacturing a gas sensor.

2. Description of the Related Art

Gas sensors are attached to an inlet system (for example, an intake pipe or an intake manifold) and an exhaust system of an internal combustion engine, such as a diesel engine or a gasoline engine, to monitor the concentration of a specific gas and to control combustion. Gas sensors that are generally used for such control have a structure in which a gas sensor element is held in a metal shell and a rear end portion of the gas sensor element is covered with a metal cover. To facilitate manufacturing and assembly of a gas sensor, a technology of attaching a resin base, instead of a metal cover, to a rear end portion of the metal shell has been developed (Japanese Patent No. 3873390, FIG. 1).

However, in the gas sensor described in Japanese Patent No. 3873390, the base has a flange; the metal shell, which faces the base, has a crimping portion; and the metal shell and the base are connected to each other by crimping the flange to the crimping portion. Therefore, the gas sensor has a problem in that it is difficult to reduce the size of the gas sensor, because the metal shell has a complex structure and the metal shell, including the crimping portion, has a large diameter. Moreover, because the base is in contact with the metal shell, heat of the metal shell is directly transferred to the base and may cause thermal degradation of the base.

SUMMARY OF THE INVENTION

An object of the present invention is to provide a gas sensor and a method of manufacturing a gas sensor with which a base, which is made of a polymer material, can be easily attached to a rear end portion of the metal shell, the productivity is improved, and the number of components is reduced.

In order to solve the problem described above, a gas sensor according to the present invention includes a gas sensor element that extends in a direction of an axis and that includes a detection portion in a front end portion thereof, the detection portion detecting a specific gas component in a gas to be measured; a metal shell that surrounds a periphery of the gas sensor element in a radial direction and that holds the gas sensor element; a base that is disposed on a rear side of the metal shell and that covers a rear end portion of the gas sensor element, the base being made of a polymer material; and a metal tube that connects the metal shell and the base to each other and that includes a rear portion and a front portion, the rear portion being integrated with the base, the front portion forming an exposed portion that is exposed from the base. A part of the exposed portion of the tube is connected to the metal shell, and the base is disposed apart from the metal shell.

With the gas sensor, by integrally forming the base with the metal tube by insert molding or the like and connecting the metal shell to the base through the tube, it is possible to easily attach the base to a rear end portion of the metal shell without forming complex structures in the metal shell and the base, and therefore the productivity can be improved. By integrally forming the base with the tube by insert molding or the like, the number of components can be reduced, the cost can be reduced, and the productivity can be further improved. As compared with, for example, a case where a flange is formed on the base and a crimping portion for crimping and fixing the flange is formed on the metal shell to connect the base to the metal shell, increase in the diameter of the metal shell can be suppressed, and reduction in the size of the gas sensor can be realized. By disposing the base apart from the metal shell by using the tube, thermal degradation of the base, which may occur when heat of the metal shell is directly transferred to the base, can be suppressed.

In the gas sensor according to the present invention, the exposed portion of the tube may extend parallel to the direction of the axis.

With the gas sensor, after integrating the base with the tube by insert molding or the like, the tube (the exposed portion) can be easily removed from a die, so that the productivity can be improved.

In the gas sensor according to the present invention, the rear portion of the tube may include a protruding portion that protrudes in the base in the radial direction.

With the gas sensor, accidental removal of the tube from the base in the direction of the axis can be suppressed.

In the gas sensor according to the present invention, the base may include a connector portion that extends in a direction that crosses the direction of the axis and that is connectable to and disconnectable from an external device, a connector terminal that is to be electrically connected to the external device is disposed in the connector portion, and the connector portion may be integrated with the connector terminal.

With the gas sensor, it is not necessary to use another component for holding the connector terminal in the base, so that the number of components can be further reduced and the cost can be further reduced. Moreover, because the tube and the connector terminal can be simultaneously fixed to the base while manufacturing the base, so that the productivity can be further improved. Because the connector portion extends in a direction that crosses the direction of the axis, when the gas sensor is attached to an intake system, the length by which the gas sensor protrudes outward from the intake system can be reduced. Thus, it is possible to sufficiently separate the gas sensor from a hood, so that safety in a vehicle crash can be improved.

The gas sensor according to the present invention may further include a sealing member that is disposed in the base so as to be in contact with a side surface of the tube.

With the gas sensor, even when the gas sensor is exposed to a high temperature and the base expands more than the tube, the sealing member seals a gap between the base and the tube, so that airtightness can be maintained.

In the gas sensor according to the present invention, the base may have an accommodation groove whose front end is open and that extends toward a rear side, at least a part of the side surface of the tube faces the accommodation groove, the sealing member may be accommodated in the accommodation groove, and the gas sensor may further include a cover that closes the accommodation groove at a position on a front side of the sealing member.

When the gas sensor is transported in a low temperature environment, the sealing member may contract and may be accidentally removed from the accommodation groove. If the sealing member is excessively compressed and accommodated in the accommodation groove to prevent this, the elasticity of the sealing member may decrease with time due to a creeping phenomenon, and the sealability may decrease. By closing the accommodation groove at a position on the front side of the sealing member, accidental removal of the sealing member can be prevented.

The gas sensor according to the present invention may further include a connection terminal that is electrically connected to the gas sensor element, and the base may be integrally formed with a separator portion that holds the connection terminal.

With the gas sensor, it is not necessary to use a separator, which is another component for holding the connection terminal, and another member (such as a metal holder having a tubular shape) for attaching the separator to the base. Therefore, the number of components can be further reduced, the cost can be further reduced, and the productivity can be further improved.

In the gas sensor according to the present invention, the connection terminal may be fitted into the separator portion.

Because the connection terminal has a complex shape, it is difficult to integrally form the base around the connection terminal by insert molding or the like. However, the connection terminal can be easily attached to the base by fitting the connection terminal to the separator portion.

A method of manufacturing a gas sensor according to the present invention is a method of manufacturing gas sensor including a gas sensor element that extends in a direction of an axis and that includes a detection portion in a front end portion thereof, the detection portion detecting a specific gas component in a gas to be measured; a metal shell that surrounds a periphery of the gas sensor element in a radial direction and that holds the gas sensor element; and a base that is disposed on a rear side of the metal shell and that covers a rear end portion of the gas sensor element, the base being made of a polymer material. The method includes insert molding the base with a metal tube, which includes a rear portion and a front portion, so that the rear portion is integrated with the base and so that the front portion forms an exposed portion that is exposed from the base; and connecting a part of the exposed portion of the tube to the metal shell so that the base is disposed apart from the metal shell.

With the method of manufacturing gas sensor, by integrally forming the base with the metal tube by insert molding or the like and connecting the metal shell to the base through the tube, it is possible to easily attach the base to a rear portion of the metal shell without forming complex structures in the metal shell and the base, and therefore the productivity can be improved. By integrally forming the base with the tube by insert molding or the like, the number of components can be reduced, the cost can be reduced, and the productivity can be further improved. As compared with, for example, a case where a flange is formed on the base and a crimping portion for crimping and fixing the flange is formed on the metal shell to connect the base to the metal shell, increase in the diameter of the metal shell can be suppressed, and reduction in the size of the gas sensor can be realized. By disposing the base apart from the metal shell by using the tube, thermal degradation of the base, which may occur when heat of the metal shell is directly transferred to the base, can be suppressed.

With the present invention, it is possible to obtain a gas sensor with which the base, which is made of a polymer material, can be easily attached to a rear end portion of the metal shell, the productivity is improved, and the number of components is reduced.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Hereinafter, an embodiment of the present invention will be described.

Figure 1:
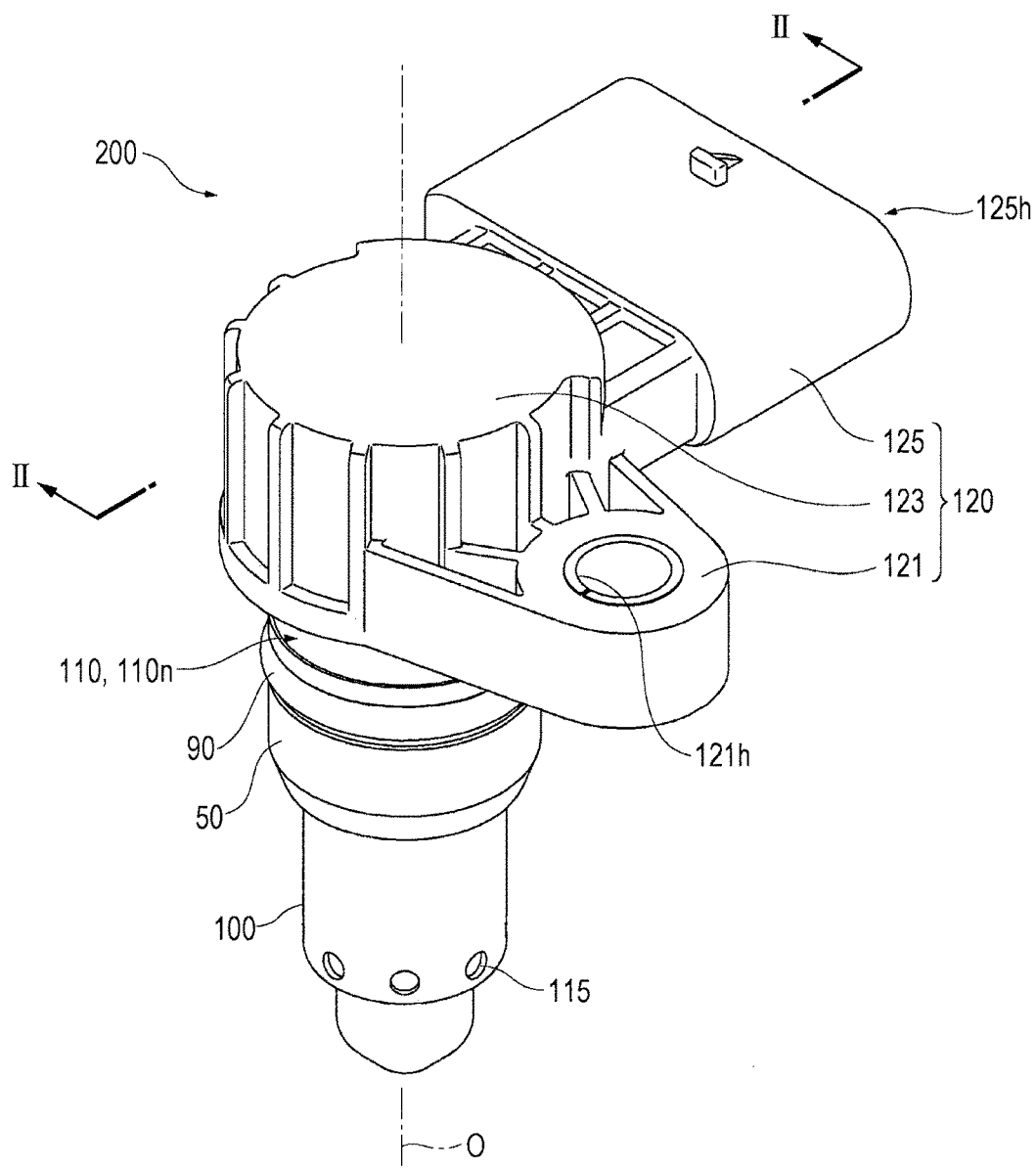
FIG. 1 is a perspective view illustrating the structure of a gas sensor according to an embodiment of the present invention.
Figure 2:
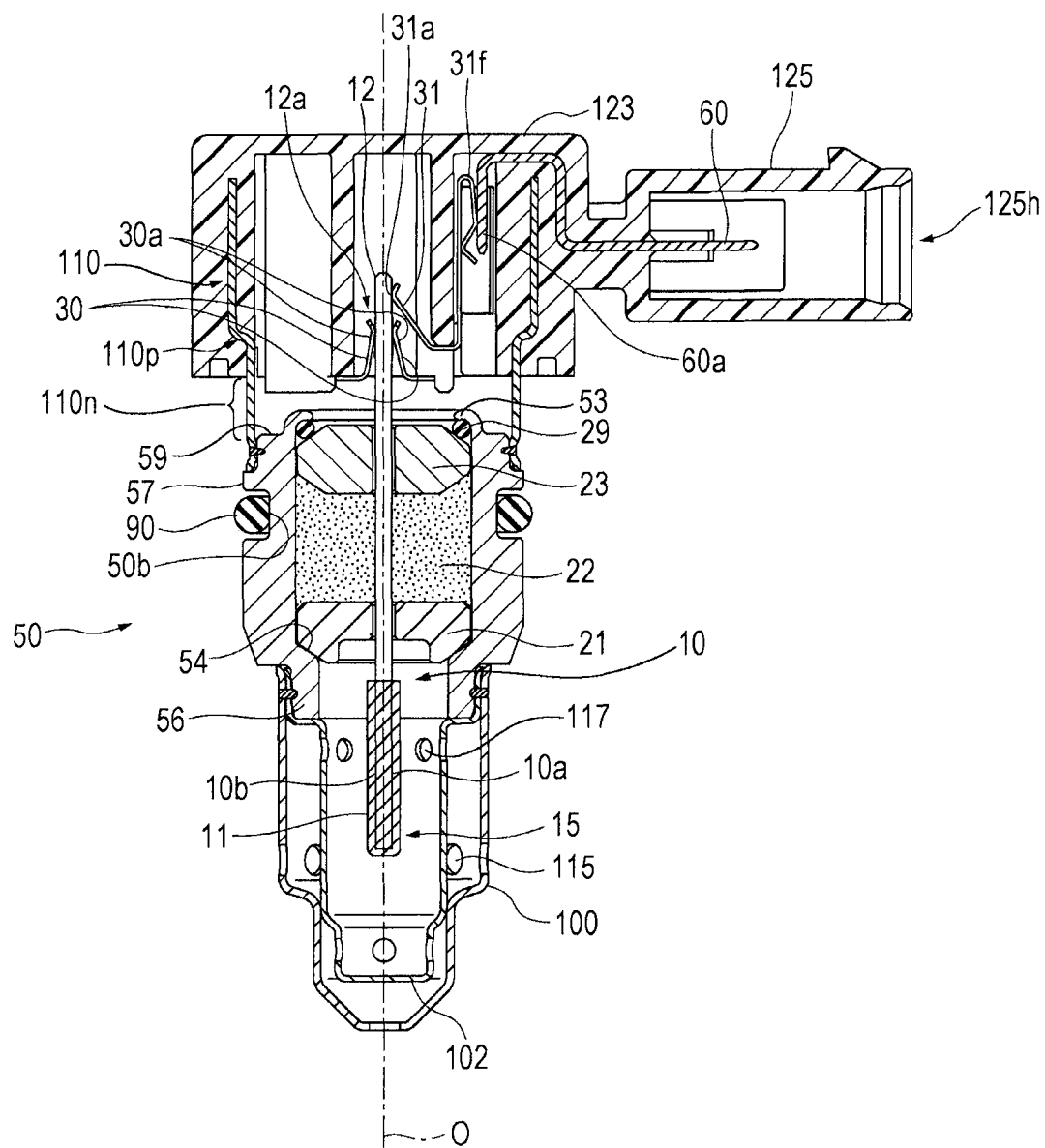
FIG. 2 is a sectional view taken along line II-II of FIG. 1.
Figure 3A:
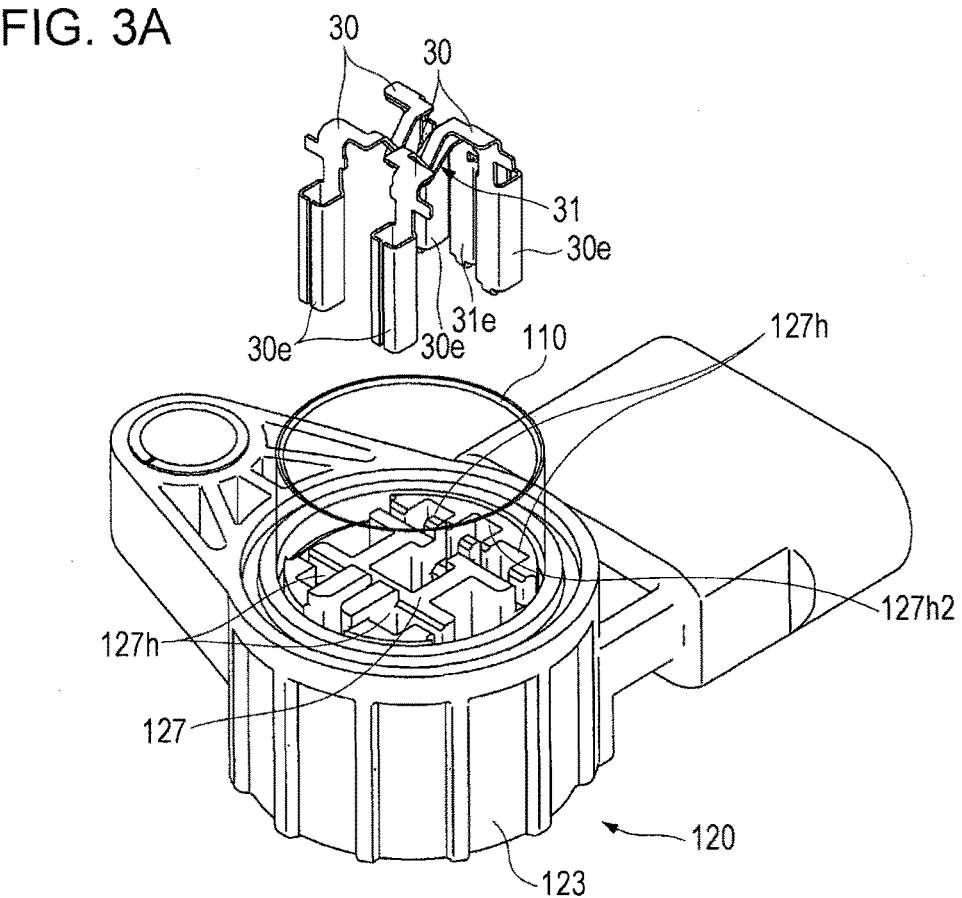
FIGS. 3A and 3B illustrate the steps of attaching connection terminals to a base.
Figure 3B:
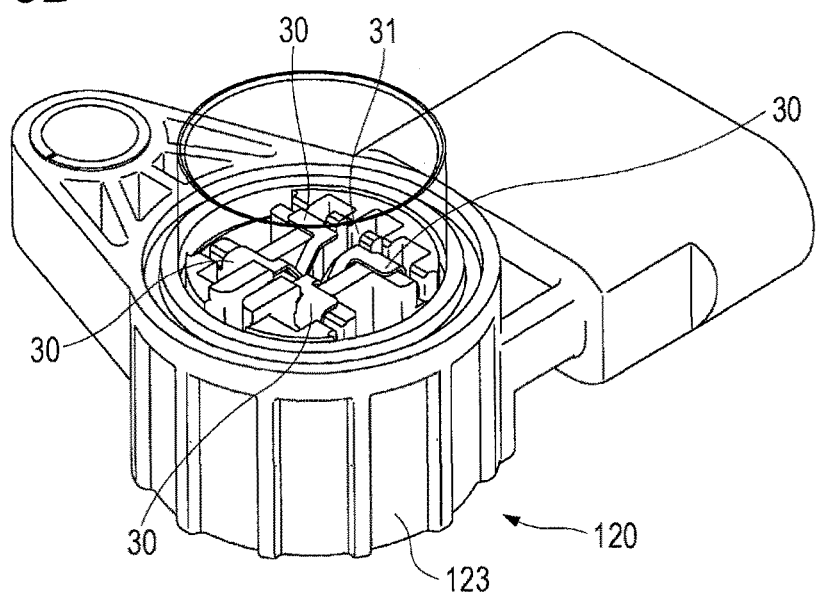

FIG. 1 is a perspective view illustrating the structure of a gas sensor 200 according to an embodiment of the present invention. FIG. 2 is a sectional view taken along line II-II of FIG. 1. FIGS. 3A and 3B illustrate the steps of attaching connection terminals 30 to a base 120. In FIGS. 3A and 3B, the front side of the base 120 faces upward.

The figures are illustrated in such a way that the direction of the axis O of a gas sensor element 10 (shown by a dashed dotted line) is the up-down direction. In the following description, a side toward a rear end portion 12 of the gas sensor element 10 will be referred to as the rear side of the gas sensor element 10 (and the gas sensor), and a side toward a detection portion 11 (see FIG. 2) of the gas sensor element 10 will be referred to as the front side of the gas sensor element 10 (and the gas sensor). A direction perpendicular to the direction of the axis O will be referred to as a "radial direction", as necessary.

In FIG. 2, for convenience of illustration, only three connection terminals and only one connector terminal are illustrated. However, in reality, there are a plurality of connection terminals and a plurality of connector terminals (five connection terminals and five connector terminals in the embodiment of the present invention).

As illustrated in FIG. 1, the gas sensor 200 includes the gas sensor element 10 (not shown), an outer protector 100 that covers the detection portion 11 of the gas sensor element 10, a metal shell 50 that holds the gas sensor element 10, the base 120 that is disposed on the rear side of the metal shell 50 and that is made of a polymer material, and a metal tube 110 that connects the metal shell 50 and the base 120 to each other.

The base 120 includes a cylindrical body 123 whose rear end is closed, a semicircular flange portion 121 extending from a side surface of the body 123 outward in a radial direction, and a substantially rectangular connector portion 125 extending from another side surface of the body 123 outward in a radial direction. The flange portion 121 and the connector portion 125 are disposed at an angle of 90 degrees in the circumferential direction of the body 123. The body 123, the flange portion 121, and the connector portion 125 are made of an easily moldable insulating polymer material (resin), such as nylon. The connector portion 125 is a male connector having an opening 125h facing outward in the radial direction. The connector portion 125 is connectable to and disconnectable from a mating connector (in this example, a female connector) of an external device in the radial direction through the opening 125h.

The flange portion 121 has a flange hole 121h. By inserting a screw (not shown) into the flange hole 121h and fastening the screw into a threaded hole in an object to which the gas sensor 200 to be attached (such as the intake system of an internal combustion engine), the gas sensor 200 can be attached to the object.

The metal shell 50 has a groove 50b (see FIG. 2) extending in the circumferential direction, and a sealing member 90 (O-ring) is fitted into the groove 50b. Accordingly, when the gas sensor 200 is inserted into an opening in the object and attached to the object, the sealing member 90 is compressed by a wall of the object and deformed, and seals a gap between the object and the gas sensor 200 (the metal shell 50).

As described below in detail, the tube 110 includes a rear portion, which is integrated with the base 120 by insert molding, and a front portion, which forms an exposed portion 110n that is exposed from the base 120. The base 120 is disposed apart from the metal shell 50 by connecting the exposed portion 110n to the rear end of the metal shell 50.

Next, referring to FIG. 2, components of the gas sensor 200 will be described further in detail.

As a known gas sensor elements, the gas sensor element 10 has a substantially prismatic shape extending in the direction of the axis O. The gas sensor element 10 is a multilayered member in which a detection element for detecting oxygen concentration and a heater for rapidly activating the detection element are bonded to each other. The detection element has a structure in which a solid electrolyte, mainly made of zirconia, and a pair of electrodes, mainly made of platinum, are stacked with an insulation layer, in which a hollow measurement chamber is formed, therebetween. To be specific, the detection element includes an oxygen pump cell and an oxygen concentration measuring cell. In the oxygen pump cell, one of a pair of electrodes on both sides of a solid electrolyte is exposed to the outside and the other electrode is disposed in a measurement chamber. In the oxygen concentration measuring cell, one of a pair of electrodes on both sides of a solid electrolyte is disposed in a measurement chamber and the other electrode is disposed on a reference gas chamber. By controlling an electric current that flows between the pair of electrodes of the oxygen pump cell so that the output voltage of the oxygen concentration measuring cell becomes a predetermined voltage, oxygen can be pumped out from the measurement chamber or oxygen can be pumped into the measurement chamber from the outside.

The detection portion 11 is a portion of the oxygen pump cell including the pair of electrode and a part of the solid electrolyte that is sandwiched between the electrodes. An electric current flows through the detection portion 11 in accordance with the oxygen concentration. Five electrode pads 12a, for outputting an output signal from the detection element and supplying electric power to the heater, are disposed on the rear end portion 12 of the gas sensor element 10. (In FIGS. 3A and 3B, two electrode pads 12a are disposed on a second surface 10b of the gas sensor element 10 and three electrode pads 12a are disposed on a first surface 10a.) These electrode pads 12a are respectively connected to the connection terminals 30 and 31 (see FIGS. 2, 3A, and 3B).

A ceramic holder 21, which has a short substantially cylindrical shape and which is made of an insulating ceramic (such as alumina), is disposed at a position that is slightly on the front side from the center of the gas sensor element 10 in the axial direction. The gas sensor element 10 extends through the ceramic holder 21, and the detection portion 11 protrudes forward from the ceramic holder 21.

The gas sensor element 10 is surrounded by the metal shell 50, which has a cylindrical shape. The metal shell 50 is made of a stainless steel, such as SUS430. To be specific, the metal shell 50 has a stepped portion 54 on the inner periphery thereof. A front peripheral edge portion of the ceramic holder 21, into which the gas sensor element 10 is inserted, is held by the stepped portion 54. Moreover, an inner space of the metal shell 50 on the rear side of the ceramic holder 21 is filled with a sealant 22 in such a way that the gas sensor element 10 extends through the sealant 22. A tubular sleeve 23 is fitted into the metal shell 50 so as to press the sealant 22 from the rear side. An annular crimping packing 29 is disposed on the outer periphery of a rear end portion of the sleeve 23.

The metal shell 50 has a rear end portion 59, which has a smaller outside diameter, near the rear end thereof; and an increased diameter portion 57, whose outside diameter increases stepwise, on the front side of the rear end portion 59. The increased diameter portion 57 has the groove 50b extending in the circumferential direction, and the sealing member 90 (O-ring) is fitted into the groove 50b. The metal shell 50 has a front engagement portion 56 on the front side of the increased diameter portion 57. The front engagement portion 56, whose outside diameter is smaller than that of the increased diameter portion 57, engages the outer protector 100 and an inner protector 102 (described below). The metal shell 50 has a crimping portion 53, for holding the gas sensor element 10 in the metal shell 50 by being crimped, on the rear side of the rear end portion 59.

The crimping portion 53 of the metal shell 50 is crimped so as to press the sleeve 23 toward the front side via the crimping packing 29. Because the crimping portion 53 is crimped, the inner space of the metal shell 50 is entirely filled with the sealant 22, which is pressed and deformed by the sleeve 23. With the sealant 22, the ceramic holder 21 and the gas sensor element 10 are positioned and airtightly held in the metal shell 50.

The outer peripheral surface of the detection portion 11 of the gas sensor element 10 is covered by a porous protective layer 15. The protective layer 15 protects electrodes of the detection portion 11, which are exposed to the outside, from poisoning and soaking due to gas intake and the like. The outer protector 100 and the inner protector 102 are fitted onto and fixed, by laser welding, to the front engagement portion 56 of the metal shell to protect the detection portion 11, which is accommodated therein. The outer protector 100 has gas inlet holes 115, and the inner protector 102 has gas inlet holes 117. Thus, adhesion of water and oil in a gas to the gas sensor element 10 is suppressed, and occurrence of a crack or breakage of the gas sensor element 10 can be suppressed. Adhesion of soot in a gas to the gas sensor element 10 can be also suppressed, and decrease in the detection accuracy of the gas sensor 200 can be suppressed.

Next, the base 120 and the tube 110 will be described.

The tube 110 is cylindrical, is made of a stainless steel or the like, and includes a rear portion having a larger diameter. This larger diameter portion is a protruding portion 110p that protrudes outward in the radial direction, (see FIGS. 3A and 3B). The base 120 is insert molded with the rear portion of the tube 110, including the protruding portion 110p. The tube 110 includes the exposed portion 110n, which is on the front side of the protruding portion 110p and which is exposed from the base 120. By fitting the front end of the exposed portion 110n onto the rear end portion 59 of the metal shell 50 and joining the front end of the exposed portion 110n to the rear end portion 59 by laser welding or the like, the base 120 is fixed to the metal shell 50 so as to be disposed apart from the metal shell 50. The base 120 serves as a cover that surrounds the rear end portion 12 of the gas sensor element 10, which protrudes on the rear side of the metal shell 50.

Connector terminals 60, to be electrically connected to an external device, are held in the connector portion 125. The connector portion 125 is insert molded with the connector terminals 60.

As illustrated in FIG. 3A, a separator portion 127, which has a substantially grid-like shape extending toward the front end, is integrally formed in the body 123. The connection terminals 30 and 31 respectively include front bent portions 30a and 31a (see FIG. 2) and base portions 30e and 31e. The front bent portions 30a and 31a are bent in an L-shape and contact the electrode pads 12a. The base portions 30e and 31e, which are substantially rectangular box-shaped, are bent toward the rear side from the front bent portions 30a and 31a. A set of three connection terminals (on the right side in FIG. 3A) is used to output an output signal from the detection element, and a set of two connection terminals (on the left side in FIG. 3A) is used to supply electric power to the heater.

As illustrated in FIG. 3B, the base portions 30e of the connection terminals 30 are fitted into four rectangular holes 127h, which are separated from each other by the separator portion 127. Likewise, the base portion 31e of the connection terminal 31 is inserted and fitted into a rectangular hole 127h2, which is separated by the separator portion 127. Thus, the connection terminals 30 and 31 are held by the separator portion 127. When the rear end portion 12 of the gas sensor element 10 is inserted into the central opening of the separator portion 127, the connection terminals 30 and 31 are electrically connected to the electrode pads 12a in such a way that the connection terminals 30 and 31 surround corresponding electrode pads 12a.

When the connection terminal 31 is inserted into the hole 127h2, a spring piece 31f, which is disposed in the bases 31e, is electrically connected to a corresponding one of end portions 60a of the connector terminals 60 (see FIG. 2). Likewise, the connection terminals 30 have similar spring pieces (not shown), and the spring pieces are electrically connected to corresponding end portions 60a of the connector terminals 60. Thus, it is possible to electrically connect the gas sensor element 10 in the gas sensor 200 to an external device.

As described above, the metal tube 110 is integrated with the base 120 by insert molding or the like, and the metal shell 50 and the base 120 are connected to each other through the tube 110. Therefore, without forming complex structures in the metal shell 50 and the base 120, the base 120 and be easily attached to a rear end portion of the metal shell 50. As a result, the productivity can be improved.

By integrating the base 120 and the tube 110 with each other by insert molding or the like, the number of components can be reduced and the productivity can be further improved. By reducing the number of components, the weight of the gas sensor can be reduced. By reducing the weight of the gas sensor, vibration of an object to which the gas sensor is attached can be reduced, and the anti-vibration ability of the gas sensor and the object to which the gas sensor is attached can be improved.

For example, as compared with a case where a flange is formed on the base 120 and a crimping portion, for crimpingly fixing the flange, is formed on the metal shell 50 in order to connect the metal shell 50 and the base 120 to each other, increase of the diameter of the metal shell 50 can be suppressed. Therefore, with the present embodiment, reduction in the size of the gas sensor can be realized.

Moreover, because the metal shell 50 and the base 120 are disposed apart from each other by using the tube 110, thermal degradation of the base 120, which may occur due to transfer of heat from the metal shell 50 to the base 120, can be suppressed.

In the present embodiment, the exposed portion 110n of the tube 110, which is exposed from the base 120 toward the front side, has a straight shape (extending parallel to the axial direction). Therefore, after the base 120 is integrated with the tube 110 by insert molding or the like, the tube 110 (the exposed portion 110n) can be easily removed from the die. In contrast, in a case where the exposed portion 110n does not have a straight shape, it is necessary to use an expensive and complex device, such as a slide die, to allow the tube 110 to be removed from the die. Therefore, the manufacturing cost is increased.

Moreover, in the present embodiment, a part of the tube 110 that is integrated with the base 120 by insert molding or the like has the protruding portion 110p, which protrudes in the radial direction. Therefore, accidental removal of the tube 110 from the base 120 in the direction of the axis O can be suppressed.

In the present embodiment, the base 120 has the connector portion 125, and the connector portion 125 is integrated with the connector terminals 60, which are disposed in the connector portion 125, by insert molding or the like. Thus, it is not necessary to use another component for holding the connector terminal 60 in the base 120, so that the number of components can be further reduced and the cost can be further reduced. Moreover, the tube 110 and the connector terminal 60 can be fixed to the base 120 while manufacturing the base 120, so that the productivity can be further improved.

In the present embodiment, the separator portion 127 is integrally formed with the base 120. Thus, it is not necessary to use a separator, which is another component for holding the connection terminals 30 and 31, and another member (such as a cylindrical metal holder) for attaching the separator to the base 120. Therefore, the number of components can be further reduced, the cost can be further reduced, and the productivity can be further improved.

Because the connection terminals 30 and 31 have complex shapes, it is difficult to form the base 120 around the connection terminals 30 and 31 by insert molding or the like. With the embodiment, the connection terminals 30 and 31 can be easily assembled with the base 120 by fitting the connection terminals 30 and 31 into the separator portion 127.

The present invention is not limited to the embodiment described above and encompasses various modifications and equivalents thereof within the spirit and scope of the present invention.

Figure 4:
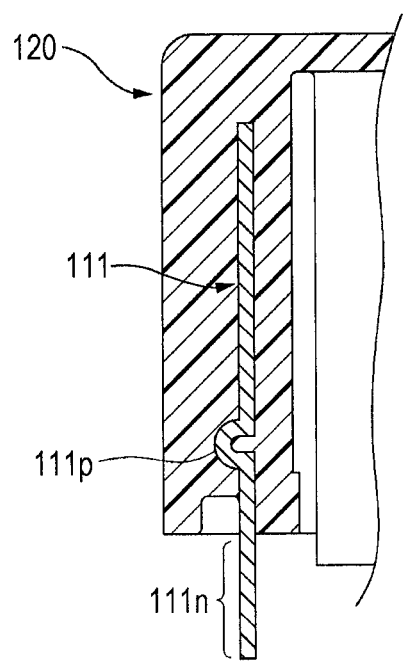
FIG. 4 is partial sectional view illustrating a modification of a tube.

For example, the protruding portion of the tube need only to protrude in the radial direction, and it is not necessary that the diameter of a rear portion of the tube be increased as in the example shown in FIG. 2. Alternatively, the diameter of a front portion of the cylindrical portion may be increased in a region in which the tube is integrated with the base by insert molding or the like. Further alternatively, as illustrated in FIG. 4, the entirety of a tube 111 may have a cylindrical shape with a uniform diameter, and a protruding portion 111$p$ may be formed by causing only a part of the tube 111, which is integrated with the base 120 by insert molding or the like, to protrude in the radial direction. Also in this case, an exposed portion 111$n$, which is a part of the tube 111 on the front side of the protruding portion 111$p$, is exposed from the base 120. The protruding portion may protrude inward in the radial direction. There may be a plurality of protruding portions arranged in the direction of the axis O.

Figure 5:
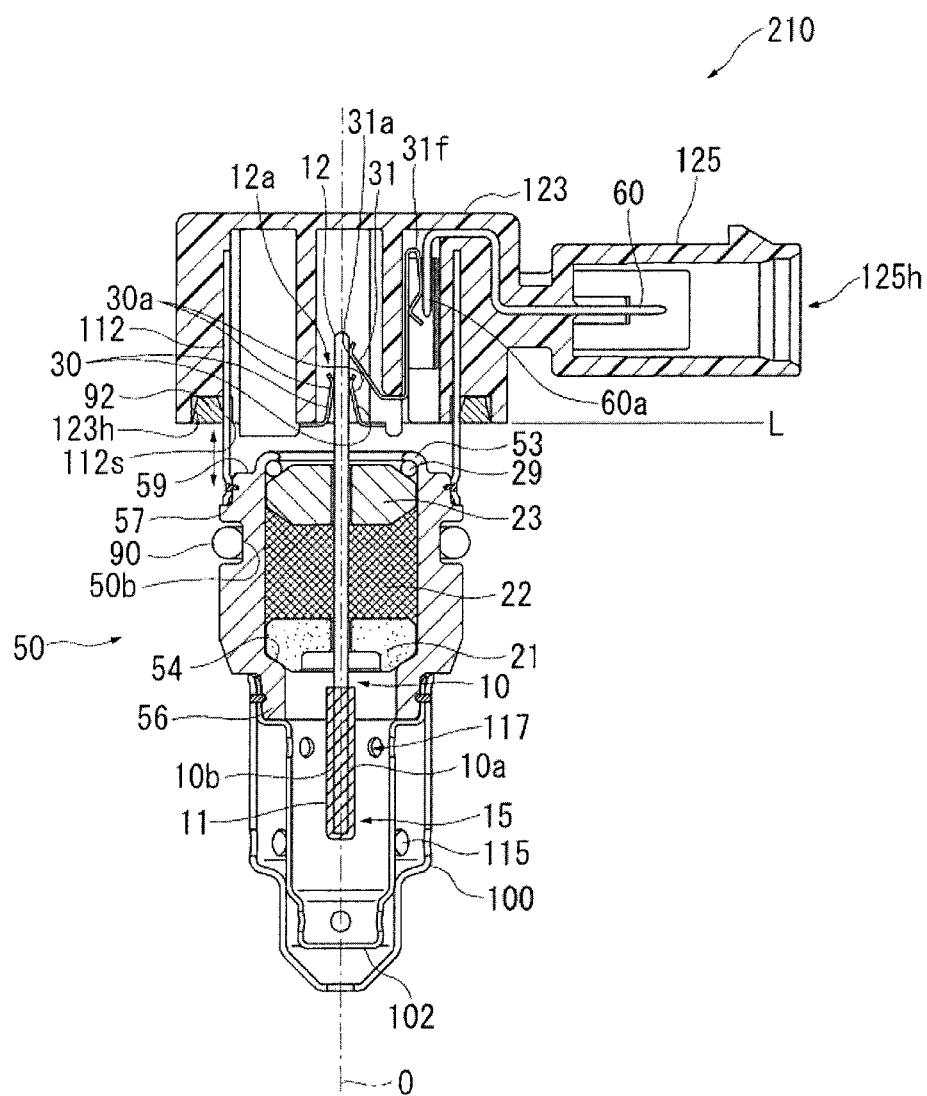
FIG. 5 is a sectional view illustrating an example in which a sealing member is disposed in a base of a gas sensor.

As illustrated in FIG. 5, a gas sensor 210 may include a sealing member 92 that is disposed in the base 120 (the body 123) so as to be in contact with a side surface of a tube 112. The gas sensor 210 differs from the gas sensor shown in FIG. 1 in that the gas sensor 210 has the sealing member 92, in that the body 123 has an accommodation groove 123$h$, and in the shape of the tube 112. In other respects, the gas sensor 210 is the same as the gas sensor 200, and components that are the same as those shown in FIG. 1 will be denoted by the same numerals and descriptions of such components will be omitted.

In FIG. 5, the tube 112 does not have a protruding portion protruding outward in the radial direction and has a straight cylindrical shape extending parallel to the direction of the axis O. The body 123 has the annular accommodation groove 123$h$ whose front end is open and that extends toward the rear side. A side surface 112$s$ on the outer side of the tube 112 faces the accommodation groove 123$h$. The sealing member 92 is accommodated in the accommodation groove 123$h$, and an inner surface of the sealing member 92 is in contact with the side surface 112$s$ on the outer side of the tube 112.

Normally, the base 120 (the body 123), which is made of a polymer material, and the tube 112, which is made of a metal, are airtightly integrated with each other by performing insert molding or the like so that the base 120 and the tube 112 are in close contact with each other along tightly-contacting surfaces thereof. However, when the gas sensor 210 is exposed to a high temperature, the base 120, which has a higher thermal expansion coefficient, expands by a larger amount and a gap may be formed between the base 120 and the tube 112.

By disposing the sealing member 92 in the base 120 (the body 123) so as to be in contact with the side surface 112$s$ of the tube 112, even when the gas sensor 210 is exposed to a high temperature, the sealing member 92 seals the gap between the base 120 and the tube 112 to ensure airtightness. A rubber O-ring can be used as the sealing member 92. Preferably, the thermal expansion coefficient of the sealing member 92 is higher than that of the base 120 (the body 123), because, in this case, sealing can be performed more reliably.

In the example illustrated in FIG. 5, an O-ring having a trapezoidal cross section is used as the sealing member 92. The O-ring is accommodated in the accommodation groove 123$h$ so that the upper surface thereof faces the rear side. The O-ring, which has a trapezoidal cross section, can be in contact with the inside of the accommodation groove 123$h$ more tightly than an O-ring having a circular cross section. Therefore, accidental removal of the O-ring from the accommodation groove 123$h$ is not likely to occur when, for example, the gas sensor 210 is transported. The front end of the sealing member 92 is substantially flush with the front surface of the body 123. After the gas sensor 210 has been attached to an object, the front surface of the body 123 serves as an attachment surface that is in contact with the front end of the sealing member 92, so that the sealing member 92 is not accidentally removed.

The side surface of the tube 112 that comes into contact with the sealing member 92 is not limited to the outer side surface and may be the inner side surface. In order that the base can be integrated with the rear portion of the tube by insert molding or the like, it is necessary that a space for accommodating the sealing member 92 (in the example shown in FIG. 5, the accommodation groove 123$h$) be an inner space whose front end is open.

When the gas sensor is transported in a low temperature environment, the sealing member 92 may contract and may be accidentally removed from the accommodation groove 123$h$. If the sealing member 92 is excessively compressed and accommodated in the accommodation groove 123$h$ to prevent this, the elasticity of the sealing member 92 may decease with time due to a creeping phenomenon, and the sealability may decrease.

Figure 6:
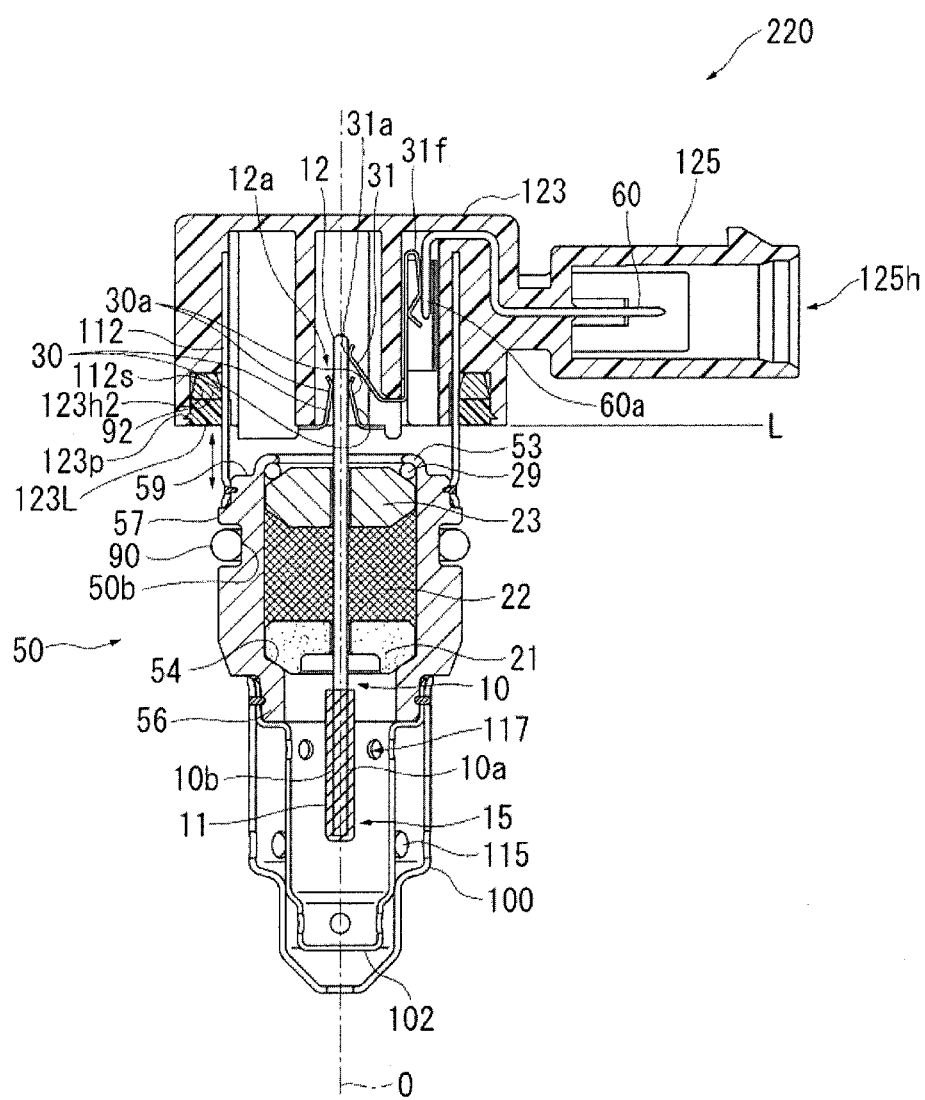
FIG. 6 is a sectional view illustrating another example in which a sealing member is disposed in a base of a gas sensor.

To prevent this, as illustrated in FIG. 6, a gas sensor 220 has an accommodation groove 123$h$2 that extends toward the rear side to a deeper position than the accommodation groove 123$h$ shown in FIG. 5. In this case, after inserting the sealing member 92 into the bottom of the accommodation groove 123$h$2, the accommodation groove 123$h$2 may be closed by a cover 123L at a position on the front side of the sealing member 92. The cover 123L may also be made of a polymer material.

For example, as illustrated in FIG. 6, an engagement protrusion 123$p$, which protrudes outward in the radial direction and decreases in diameter toward the rear side, may be formed on the outer side surface of the cover 123L. By engaging the engagement protrusion 123$p$ with the outer side surface of the accommodation groove 123$h$2, accidental removal of the cover 123L can be prevented. The cover 123L may be press-fitted into the accommodation groove 123$h$2.

In the embodiment described above, the sensor element is a strip-shaped element having a rectangular cross section. However, the cross-sectional shape of a sensor element used in a gas sensor according to the present invention may be a square shape or any other appropriate shape. The gas sensor according to the embodiment described above is a wideband air fuel ratio sensor. However, a gas sensor according the present invention may be a gas sensor of a different type.

What is claimed is:
1. A gas sensor comprising:
  a gas sensor element that extends in a direction of an axis and that includes a detection portion in a front end portion thereof, the detection portion detecting a specific gas in a mixed gas;
  a metal shell that surrounds a periphery of the gas sensor element in a radial direction to hold the gas sensor element;
  a base that is disposed on a rear side of the metal shell and that covers a rear end portion of the gas sensor element, the base being made entirely of a polymer material; and
  a metal tube that connects the metal shell and the base to each other and that includes a rear portion and a front portion, the rear portion being integrated with and embedded inside the base such that an outer surface of the rear portion abuts the base, the front portion having an exposed portion that is exposed from the base, wherein a part of the exposed portion of the tube is connected to the metal shell, and the base is disposed apart from the metal shell.

2. The gas sensor according to claim 1, wherein the exposed portion of the tube extends parallel to the direction of the axis.

3. The gas sensor according to claim 1, wherein the rear portion of the tube includes a protruding portion that protrudes in the base in the radial direction.

4. The gas sensor according to claim 1, wherein the base includes a connector portion that extends in a direction that crosses the direction of the axis and that is removably connected to an external device, and wherein the connector portion contains a connector terminal that is electrically connected to the external device, and the connector portion is integrated with the connector terminal.

5. The gas sensor according to claim 1, further comprising:
a sealing member that is disposed in the base so as to be in contact with a side surface of the tube.

6. The gas sensor according to claim 5, wherein
the base has an accommodation groove whose front end is open and that extends toward a rear side,
at least a part of the side surface of the tube faces the accommodation groove,
the sealing member is accommodated in the accommodation groove, and
the gas sensor further includes a cover that closes the accommodation groove at a position on a front side of the sealing member.

7. The gas sensor according to claim 1, further comprising:
a connection terminal that is electrically connected to the gas sensor element,
wherein the base is integrally formed with a separator portion that holds the connection terminal.

8. The gas sensor according to claim 7, wherein the connection terminal is fitted into the separator portion.

9. The gas sensor according to claim 1, wherein the detection element is provided at a distance from the base so as not to abut the base.

10. A method of manufacturing a gas sensor including
a gas sensor element that extends in a direction of an axis and that includes a detector in a front end portion thereof, the detector detecting a specific gas in a mixed gas;
a metal shell that surrounds a periphery of the gas sensor element in a radial direction to hold the gas sensor element; and
a base that is disposed on a rear side of the metal shell and that covers a rear end portion of the gas sensor element, the base being made entirely of a polymer material;
the method comprising the step of:
insert molding the base with a metal tube, which includes a rear portion and a front portion, so that the rear portion is integrated with and embedded inside the base such that an outer surface of the rear portion abuts the base and the front portion has an exposed portion that is exposed from the base; and
connecting a part of the exposed portion of the tube to the metal shell so that the base is disposed apart from the metal shell.

* * * * *